(12) United States Patent
Jaeger et al.

(10) Patent No.: US 12,345,693 B2
(45) Date of Patent: Jul. 1, 2025

(54) COMPUTER-ASSISTED METHOD FOR GENERATING TRAINING DATA FOR A NEURAL NETWORK FOR PREDICTING A CONCENTRATION OF POLLUTANTS AT A MEASURING STATION

(71) Applicant: Siemens Aktiengesellschaft, Munich (DE)

(72) Inventors: Florian Ansgar Jaeger, Berlin (DE); Katrin Müller, Berlin (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 406 days.

(21) Appl. No.: 17/924,281

(22) PCT Filed: May 6, 2021

(86) PCT No.: PCT/EP2021/061978
§ 371 (c)(1),
(2) Date: Nov. 9, 2022

(87) PCT Pub. No.: WO2021/228675
PCT Pub. Date: Nov. 18, 2021

(65) Prior Publication Data
US 2023/0184730 A1    Jun. 15, 2023

(30) Foreign Application Priority Data

May 13, 2020   (DE) .................... 10 2020 206 047.9

(51) Int. Cl.
*G01N 33/00*   (2006.01)
*G06N 3/08*    (2023.01)

(52) U.S. Cl.
CPC .......... *G01N 33/0034* (2013.01); *G06N 3/08* (2013.01)

(58) Field of Classification Search
CPC ............................. G01N 33/0034; G06N 3/08
See application file for complete search history.

(56) References Cited

U.S. PATENT DOCUMENTS

| | | | |
|---|---|---|---|
| 2012/0024041 A1 | 2/2012 | Morris | 73/19.01 |
| 2018/0081999 A1 | 3/2018 | Chappell | |
| 2018/0321208 A1 | 11/2018 | Bai | G01N 33/00 |

FOREIGN PATENT DOCUMENTS

| | | | |
|---|---|---|---|
| CN | 108491970 A | 9/2018 | |
| EP | 3 627 403 | 3/2020 | G06N 7/00 |
| EP | 3 629 263 | 4/2020 | G06Q 10/06 |

OTHER PUBLICATIONS

Byliński H, Kolasińska P, Dymerski T, Gębicki J, Namieśnik J. Determination of odour concentration by TD-GC×GC-TOF-MS and field olfactometry techniques. Monatsh Chem. 2017;148(9):1651-1659. (Year: 2017).*

(Continued)

*Primary Examiner* — Daniel R Miller
*Assistant Examiner* — George O Sahyoun
(74) *Attorney, Agent, or Firm* — Slayden Grubert Beard PLLC

(57) ABSTRACT

Various embodiments of the teachings herein include a computer aided method for generating training data for a neural network designed to determine a pollutant concentration at a measurement station from a pollutant emission. The method may include: providing a measurement series of the concentration containing a value above a threshold; providing a measurement series for a variable related to the pollutant concentration; providing a transmission model modelling a relationship between the pollutant emission, the measured variable, and the pollutant immission at the measurement station; computing a first value of the pollutant immission using the transmission model using a value of the measured variable; computing a second value of the pollut- (Continued)

ant immission using the transmission model by numerically altering the measured value of the measured variable; and generating a synthetic measurement series as training data by an alteration based at least in part on a relative change in computed values.

9 Claims, 1 Drawing Sheet

(56) References Cited

OTHER PUBLICATIONS

Warmiński K, Bęś A. Atmospheric Factors Affecting a Decrease in the Night-Time Concentrations of Tropospheric Ozone in a Low-Polluted Urban Area. Water Air Soil Pollut. 2018;229(11):350. (Year: 2018).*

Byliński H, Barczak RJ, Gębicki J, Namieśnik J. Monitoring of odors emitted from stabilized dewatered sludge subjected to aging using proton transfer reaction-mass spectrometry. Environ Sci Pollut Res Int. Feb. 2019;26(6):5500-5513. (Year: 2019).*

Search Report for International Application No. PCT/EP2021/061978, 11 pages, Aug. 13, 2021.

Search Report for DE Application No. 10 2020 206 047.9, 4 pages, Jan. 19, 2021.

Zheng Yu et al: "Forecasting Fine-Grained Air Quality Based on Big Data"; Hot Topics in Middleboxes and Network Function Virtualization, ACM, pp. 2267-2276, Aug. 10, 2015.

Xu, Yanan et al., "When Remote Sensing Data meet Ubiquitous Urban Data: Fine-Grained Air Quality Inference," 2016 IEEE International Conference on Big Data (Big Data), pp. 1252-1261.

Yongquan, Wan et al., "An Air Quality Prediction Method Integrating Meteorological Parameters and Pollutant Concentrations," Computer Applications and Software, vol. 35, No. 8, pp. 113-117 (Chinese w/ English abstract).

Gu, Ke et al., "Recurrent Air Quality Predictor Based on Meteorology- and Pollution-Related Factors," IEEE Transactions on Industrial Informatics, vol. 14, No. 9, pp. 3946-3955.

Chinese Office Action, Application No. 202180034346.1, 11 pages.
Indian Office Action, Application No. 202217059612, 6 pages.

* cited by examiner

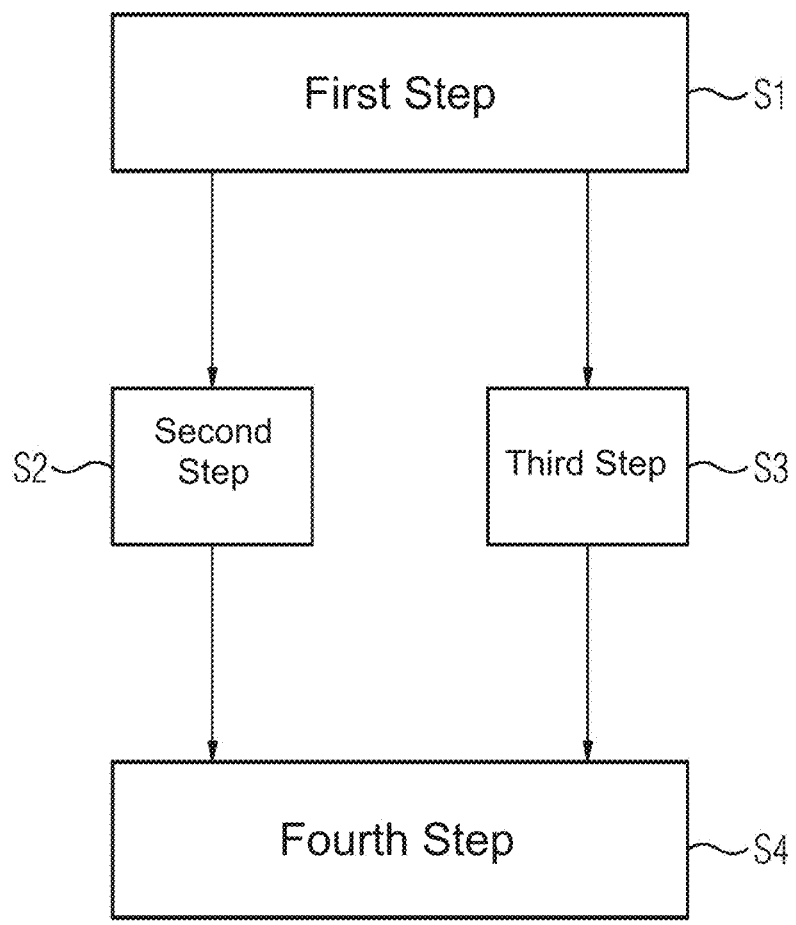

COMPUTER-ASSISTED METHOD FOR GENERATING TRAINING DATA FOR A NEURAL NETWORK FOR PREDICTING A CONCENTRATION OF POLLUTANTS AT A MEASURING STATION

CROSS-REFERENCE TO RELATED APPLICATIONS

This application is a U.S. National Stage Application of International Application No. PCT/EP2021/061978 filed May 6, 2021, which designates the United States of America, and claims priority to DE Application No. 10 2020 206 047.9 filed May 13, 2020, the contents of which are hereby incorporated by reference in their entirety.

TECHNICAL FIELD

The present disclosure relates to neural networks. Various embodiments include methods and/or systems for generating training data for a neural network.

BACKGROUND

The pollutant burden, for example a nitrogen oxide concentration, can be above the permissible limit values within some German cities for specific periods of time. To guarantee adequate air quality, cities can take several measures, for example bans on driving. For these measures to be effective, however, it is necessary for them to be carried out even before the limit values are possibly exceeded. This requires a prediction (forecast) of the pollutant concentration that is reliable and as precise as possible.

In principle, a distinction is drawn between emissions and immissions (mass or mass per length per time dimension) and concentrations (mass per volume dimension). The emission is the emitted mass of a pollutant, for example from a road user within a time range, for example one hour. The emission may likewise relate to a length (road length, route length, etc.) and a time range, with the result that it comprises the dimension mass per length per time in this instance. The pollutant concentration is measured by a measurement station, for example, at a specific location within the town, based on the immission present there. In principle, the emissions, immissions and pollutant concentrations are time dependent.

The pollutant concentration is difficult to predict owing to the complexity of the processes, with the result that neural networks are typically used for this purpose. The fundamental method is split in two in this instance. First, the emission is computed by means of a model. The pollutant concentration is then determined by means of the neural network from the emission computed on a model basis.

This requires the neural network to be trained, that is to say that training data concerning the pollutant concentration are required. Symbolically, the neural network needs to use the training data to learn how the pollutant concentration results from the pollutant emission. Typically, the neural network is trained by using historical data of the pollutant concentration as training data. A neural network trained in this manner provides a good prediction in situations that occur frequently.

It is therefore possible for the average pollutant concentration to be predicted with sufficient accuracy by said prediction.

Events or situations involving a heavy burden are problematic because they are typically rare. As a result, only few data are available for training the neural network. This problem means that the prediction is poorer for the events involving a heavy burden that are actually of interest, that is to say for the rare events.

Essentially two methods to improve the prediction for rare events such as these are known from the prior art. First, the data or measurement series used for training can be weighted differently. By way of example, a historical event involving a heavy burden is used repeatedly. The disadvantage of this is that it impairs the prediction of the average burden. The actual problem that fewer measurement series or measurement data and hence training data are available for events involving a heavy burden therefore persists. Second, the pollutant emission and pollutant concentration can be computed by a complete model based approach. This is a large amount of effort, and also not all dependencies are known. The known methods therefore typically provide excessively low values for the pollutant concentration.

SUMMARY

The teachings of the present disclosure include improved training of a neural network provided for determining a pollutant concentration from a pollutant emission. For example, some embodiments include a computer aided method for generating training data for a neural network, wherein the neural network is designed to determine a pollutant concentration at a measurement station from at least one pollutant emission, characterized by the following steps: providing at least one measurement series of the pollutant concentration containing at least one measured value that is above a defined threshold value; providing at least one measurement series for a physical measured variable related to the measured pollutant concentration, in particular a temperature, a wind speed and/or a wind direction and/or chemical substance concentrations; providing a transmission model, wherein the transmission model models a relationship between the pollutant emission, the measured variable and the pollutant immission at the measurement station; computing a first value $I_0$ of the pollutant immission by means of the transmission model from the pollutant emission, this being accomplished by using at least one measured value of the measured variable that is related to a value $C_0$ of the provided measured pollutant concentration; computing a second value $I_1$ of the pollutant immission by means of the transmission model from the pollutant emission, this being accomplished by numerically altering the measured value of the measured variable that is used for computing the first value $I_0$ of the pollutant immission; and generating a synthetic measurement series as training data by means of an alteration $\Delta_C$ of the value $C_0$ of the provided measured measurement series of the pollutant concentrations, the alteration $\Delta_C$ being made by means of the relative change $\Delta I/I_0$ in the computed values of the pollutant emissions.

In some embodiments, the alteration $\Delta_C$ of the at least one value $C_0$ of the provided measurement series of the pollutant concentrations is additionally made by means of a traffic-related proportion $\alpha$ of the pollutant concentration.

In some embodiments, the alteration $\Delta_C$ of the at least one value $C_0$ of the provided measurement series of the pollutant concentration is made by means of $\Delta C/C_0 = \alpha \Delta I/I_0$.

In some embodiments, a traffic-related proportion $\alpha$ in the range from 0.3 to 0.5 is used.

In some embodiments, a nitrogen oxide concentration is used as pollutant concentration and a nitrogen oxide emission is used as pollutant emission.

In some embodiments, the physical measured variable used is/are a temperature, a wind speed, a traffic level and/or one or more chemical substance concentrations.

In some embodiments, the measurement series of the pollutant concentration and the measurement series of the measured variable were captured by means of a measurement station within a town.

In some embodiments, the transmission model used is a model which takes into account a chemical composition of the air and/or chemical reactions within the air.

In some embodiments, the neural network is designed to determine a pollutant concentration from at least one pollutant emission, characterized in that a training dataset generated as claimed in one of the preceding claims is used to train the neural network.

As another example, some embodiments include a computer aided method for determining a pollutant concentration by means of a neural network and by means of a domain model of the pollutant emission, wherein the neural network is designed to determine a pollutant concentration from the pollutant emission and is trained as claimed in claim 8, wherein the domain model models a relationship between a physical measured variable, in particular a temperature, a wind speed and/or a traffic level, and the pollutant emission, characterized by the following steps: computing a value of the pollutant emission by means of the domain model, this being accomplished by using at least one measured value of the measured variable; and determining the pollutant concentration from the computed value of the pollutant emission by means of the neural network.

BRIEF DESCRIPTION OF THE DRAWINGS

Further advantages, features, and details of the teachings herein can be obtained from the exemplary embodiments described below and from the drawing. The single FIGURE of said drawing shows a schematic flowchart for a configuration of the invention. Elements that are of the same type, are equivalent or have the same effect may be provided with the same reference signs in the FIGURE.

The FIGURE shows a flowchart, or flow diagram, of a method incorporating teachings of the present disclosure.

DETAILED DESCRIPTION

The teachings of the present disclosure include computer aided methods and/or systems for generating training data for a neural network, wherein the neural network is designed to determine a pollutant concentration at a measurement station from at least one pollutant emission. In some embodiments, the method includes: providing at least one measurement series of the pollutant concentration containing at least one measured value that is above a defined threshold value; providing at least one measurement series for a physical measured variable related to the measured pollutant concentration, in particular a temperature, a wind speed and/or a wind direction and/or chemical substance concentration; providing a transmission model, wherein the transmission model models a relationship between the pollutant emission, the measured variable and the pollutant immission at the measurement station; computing a first value $I_0$ of the pollutant immission by means of the transmission model from the pollutant emission, this being accomplished by using at least one measured value of the measured variable that is related to a (original) value $C_0$ of the provided measured pollutant concentration; computing a second value $I_1$ of the pollutant immission by means of the transmission model from the pollutant emission, this being accomplished by numerically altering the measured value of the measured variable that is used for computing the first value $I_0$ of the pollutant immission; and generating a synthetic measurement series as training data by means of an alteration $\Delta_C$ of the value $C_0$ of the provided measured measurement series of the pollutant concentrations, the alteration $\Delta_C$ being made by means of the relative change $\Delta I/I_0$ in the computed values of the pollutant emissions.

The methods and systems described herein for generating training data provides data, or a time series, of the pollutant concentration, which can be used to train the neural network. The training can be effected by means of known methods, for example deep learning. The neural network (artificial neural network) may be used to determine a pollutant concentration from a pollutant emission at the measurement station. The pollutant immission, or the pollutant immissions, are computed by means of the transmission model from the pollutant emission, or pollutant emissions. The transmission model thus models the transportation of the emitted pollutants from the emission location, for example a road, to the immission location, i.e. to the measurement point. The transmission model can preferably comprise chemical conversion processes and associated equations.

In some embodiments, the method uses a measurement series of a pollutant concentration, wherein at least one value, or measured value, of the pollutant concentration is above the defined threshold value. In other words, a measurement series is provided that corresponds to a pollutant concentration that is high at at least one time and therefore to a heavy pollutant burden. A rare event of a heavy pollutant burden had therefore occurred.

The threshold value is typically defined by a limit value, for example 200 micrograms per cubic meter ($\mu g/m^3$) for nitrogen oxide. The measurement series is a chronological sequence (continuous or discrete) of measured values of the pollutant concentration, for example in the unit $\mu g/m^3$. The measurement series comprises one or more measured values, each measured value having been captured at a specific time. The time can likewise be a time range, with the result that a measured value was captured or determined for the time range. By way of example, a measured value of the pollutant concentration is determined for each hour, for example by one or more measurements. In other words, a measured value of the pollutant concentration is captured for each hour of a day, for example. The chronologically ordered sequence of these captured measured values then forms an exemplary measurement series of the pollutant concentration.

In some embodiments, the method includes generating the training data, at least one measurement series of a physical/technical measured variable is provided. In this case, the measured variable is a physical/technical variable, for example a temperature, a wind speed and/or a wind direction and/or one or more chemical substance concentrations. The measured variable is related to the provided measured pollutant concentration, that is to say that a measured value of the pollutant concentration and a measured value of the measured variable are available for each time. There may be provision for multiple measured variables and corresponding measurement series.

By way of example, an average pollutant concentration and the average temperature, wind speed and/or wind direction prevailing for the respective average pollutant concentration, and therefore related, are captured for each hour of a day. In other words, at least two measured variables are captured over time, the pollutant concentration and the physical/technical measured variable, for example the temperature, the wind speed and/or the wind direction that are or were prevailing for the measured pollutant concentration. The measured variable is significant because it or multiple measured variables, such as for example temperature, wind speed and/or wind direction and/or a chemical composition of the air (chemical substance concentrations), fundamentally influence the pollutant concentration, that is to say that the pollutant concentration is dependent on the one or more measured variables. As such, the pollutant concentration at the measurement station within a town can be decisively dependent on wind direction and/or wind speed and chemical composition of the air.

In some embodiments, the method includes a the transmission model, wherein the transmission model models, or describes, a relationship (dependency) between the pollutant emission, the measured variable and the pollutant immission at the measurement station. The transmission model can therefore be used to compute the pollutant immission, for example of road users, on the basis of the measured variable, for example temperature, wind speed and/or wind direction and/or chemical substance concentrations. These transmission models are typically complex and additionally comprise equations relating to chemical conversion processes within the air. The transmission model therefore comprises input variables and at least one output variable, the input variables being the pollutant emission and measured variable and the output variable being the pollutant immission at the measurement station.

In some embodiments, the method includes computing a first value $I_0$ of the pollutant immission by means of the transmission model from the pollutant emission. This is accomplished by using at least one measured value of the measured variable that is related to a value $C_0$ of the provided measured pollutant concentration. In other words, the value of the measured variable that is related to the value $C_0$ of the provided measured pollutant concentration, for example the value of the temperature that is related to the value of the pollutant concentration, is used as an input variable for the model. The further input variable is the pollutant emission which can also be computed. From this, the transmission model then computes the first value $I_0$ of the pollutant immission. By way of example, temperature, wind speed and/or wind direction are put into the transmission model as input variables, from which the transmission model then computes the first pollutant immission $I_0$ at the measurement station or in a region of the measurement station.

In some embodiments, the method includes computing a second value $I_1$ of the pollutant immission by means of the transmission model, based on the same pollutant emissions. The pollutant emissions thus remain unaltered. However, the measured value of the measured variable that is used for computing the first value $I_0$ of the pollutant immission is numerically altered. In other words, the second pollutant immission $I_1$ is computed for an altered value of the measured variable, for example for an altered value of temperature, wind speed and/or wind direction and/or altered substance concentrations of chemical substances in the air, for example nitrogen oxides, oxygen and/or ozone.

The altered value of the measured variable or accordingly the altered measurement series of the measured variable is therefore put into the transmission model as an input variable. As a result, the second value of the pollutant immission $I_1$, or a second pollutant immission, or a second time series of the pollutant immission, is computed. With this in mind, the second value of the pollutant immission $I_1$ corresponds to a synthetic pollutant immission that would prevail for a corresponding altered value of the measured variable, for example for an altered temperature, an altered wind speed and/or an altered wind direction and/or altered chemical boundary conditions. In this case, it is advantageous to alter the value of the measured variable only slightly. By way of example, the relative change in the value of the measured variable is preferably less than 10 percent.

In some embodiments, the method includes generating a new, further or synthetic measurement series, on which the training dataset is based. In other words, the training dataset comprises the new measurement series, the neural network being trainable or being trained or having been trained by means of the new measurement series. The new measurement series is generated by means of an alteration $\Delta_C$ of the value $C_0$ of the provided measured measurement series of the pollutant concentrations, the alteration $\Delta_C$ being made by means of the relative change $\Delta I/E_0=(I_1-I_0)/I_0$ in the computed values of the pollutant immissions.

All the equations mathematically equivalent to the stated relative change are likewise included here. Since the new measurement series is based on the second (synthetically) computed value $I_1$ of the pollutant immission, and the second value $I_1$ is certainly not based on a measured value of the measured variable, the new, or further, measurement series of the pollutant concentration can likewise be referred to as a synthetic measurement series. In other words, the freshly generated measurement series for the provided measured measurement series has not been measured, but rather has been generated synthetically by means of the described method.

The teachings of the present disclosure therefore allow a plurality of synthetic measurement series of the pollutant concentration to be generated, which can be used to train the neural network, as with the originally measured measurement series of the pollutant concentration already. Since the original provided measured measurement series of the pollutant concentration and thus also the associated measured values of the measured variable and the pollutant emission correspond or led to a rare event involving a heavy burden—this being guaranteed by the threshold value of the first step of the present method—it is therefore possible to generate multiple measurement series of rare events involving a heavy burden synthetically. This is therefore the case since the measured value of the measured variable is altered starting from the actual measured value measured when the rare event occurs. If the neural network is trained by means of these freshly generated synthetic measurement series, the prediction of the neural network for said rare events is improved without needing to expect a deterioration in the average response. As a result, high values of the pollutant concentration can be predicted in an improved manner.

In other words, the teachings of the present disclosure allow the neural network to learn from a more extensive training dataset. This improves the prediction of the neural network with regard to the rare, but most relevant, events involving a heavy burden. Furthermore, the integration of the prediction algorithm into already existing models is no more complex than the use of conventional algorithms for neural networks. This is the case because although these are improved, their structure remains unchanged. In other words, the present disclosure relates first of all to the training of the neural network, or the generation of a related training dataset, or extension of an already existing training dataset.

In comparison with a weighting of measured values, it is likewise possible to produce a much better database. Compared to a complete model based approach, the effort and data requirement are much lower. Furthermore, the transmission model does not have to be operated online for a prediction, but rather merely needs to run for the specific and relevant events or scenarios for training the neural network. This allows processing time to be saved. There can be provision for an online mode, however.

The teachings of the present disclosure allow a more accurate prediction for lower effort and reduced data requirements. In some embodiments, a computer aided method for training a neural network designed to determine a pollutant concentration from at least one pollutant emission, is characterized in that a training dataset generated and/or one of its configurations is used to train the neural network. Similar and equivalent advantages and configurations are obtained for the methods described herein for generating the training data.

In some embodiments, a computer aided method for determining a pollutant concentration by means of a neural network and by means of a domain model of the pollutant emission, wherein the neural network is designed to determine a pollutant concentration from the pollutant emission and is trained, wherein the domain model models a relationship between a physical/technical measured variable, in particular a temperature, a wind speed and/or a traffic level, and the pollutant emission, is characterized by the following steps: computing a value of the pollutant emission by means of the domain model, this being accomplished by using at least one measured value of the measured variable; and determining the pollutant concentration from the computed value of the pollutant emission by means of the neural network.

In some embodiments, the methods provide a prediction for the pollutant concentration. The prediction corresponds to the determined pollutant concentration. Based on the determined pollutant concentration, there may be provision for technical measures that lead to an actual reduction in the pollutant concentration. The prediction can already provide for and/or propose such automated measures. By way of example, one such measure could be traffic being diverted by appropriate traffic lights and/or roads being closed completely. Moreover, more buses and/or trams could be made available in an automated manner and on the basis of the prediction according to the invention. Similar and equivalent advantages and configurations are obtained for the method for generating the training data, or for the neural network trained as described herein.

In some embodiments, the alteration $\Delta_C$ of the at least one value $C_0$ of the provided measurement series of the pollutant concentrations is additionally made by means of a traffic-related proportion $\alpha$ of the pollutant concentration. In other words, the traffic-related proportion of the pollutant concentration is taken into consideration. The pollutant concentration of a pollutant, for example nitrogen oxide, is typically made up of multiple proportions. The proportions are primarily traffic, buildings and industry and also power generation. The traffic proportion, that is to say the traffic-related proportion $\alpha$, is typically known. For example as a result of a comparison with another measurement station, which is not as heavily burdened by traffic. This advantageously allows the pollutant immission or pollutant concentrations to be inferred from the pollutant emissions in an efficient manner without requiring explicit and complex computation or determination. This approximative heuristic approach therefore allows efficient determination of the pollutant concentrations from the pollutant emissions and therefore provision, or generation, of the training dataset.

In some embodiments, the alteration $\Delta_C$ of the at least one value $C_0$ of the provided measurement series of the pollutant concentration is made by means of $\Delta C/C_0 = \alpha \Delta I/I_0$. In other words, a linear dependency between the relative change in the pollutant immissions and the relative change in the pollutant concentrations is preferably used. The relative change in the pollutant immissions is determined according to the present invention by the transmission model. That is to say that, based on a measured value of the measured variable, for example temperature, wind speed and/or wind direction and/or chemical substance concentrations, this measured variable has its value altered, and a new pollutant immission related to the altered measured value is determined and the relative change between the new pollutant immission (second pollutant immission) and the pollutant immission related to the original measured value of the measured variable (first pollutant immission) is computed.

The pollutant concentration required for training the neural network is ascertained by means of the traffic-related proportion $\alpha$ from the thus determined relative change in the pollutant immissions. This is carried out in particular for each value, or time, of the original measurement series of the pollutant concentrations. In other words, each value $C_0$ of the measurement series of the pollutant concentration is altered by a typically different $\Delta C$. The value $C_1$ of the thus freshly formed synthetic measurement series of the pollutant concentration is accordingly determined for each time t by $C_1(t) = C_0(t) + \Delta C(t)$, or for discrete time values $t_n$ by $C_1(t_n) = C_0(t_n) + \Delta C(t_n)$. It is likewise possible to alter only subranges of the measurement series of the pollutant concentration in such a way, in particular just one value, or time, of said measurement series. There may be provision for further mathematically equivalent formulations and/or changes.

In some embodiments, a traffic-related proportion $\alpha$ in the range from 0.3 to 0.5 is used. In other words, traffic, which comprises road traffic, for example, has a proportion of the pollutant concentration, for example at a measurement station on a road, in the range from 0.3 to 0.5. A high local traffic-related proportion (traffic proportion) may be appropriate. The traffic-related proportion $\alpha$ is fundamentally dependent on the circumstances of the individual case, for example the town, the road, the location of the measurement station, etc. Nevertheless, it has been found that high local traffic-related proportions, at best in combination with as homogeneous an urban background as possible, are particularly well suited to determining the relative change in the pollutant concentration from the relative change in the pollutant immissions.

In some embodiments, a nitrogen oxide concentration is used as pollutant concentration and a nitrogen oxide emission is used as pollutant emission. In other words, the pollutant under consideration is nitrogen monoxide and/or nitrogen dioxide (in summary $NO_x$). In some embodiments, there may be further nitrogen oxide compounds. There may likewise alternatively or additionally be further pollutants. As such, the teachings of the present disclosure can be used for a plurality of pollutants or pollutant classes. In particular likewise for particle classes of pollutants, for example $PM_{10}$ and/or $PM_{2.5}$. The transmission model can comprise chemical conversion processes of nitrogen oxides and/or further chemical substances. In particular the chemical conversion processes based on solar radiation are included.

In some embodiments, the physical/technical measured variable used is/are a temperature, a wind speed and/or a traffic level and/or one or more substance concentrations. Temperature, wind speed and/or traffic level and/or chemical substance concentrations are technically relevant variables, in particular temperature, wind direction/wind speed and/or solar radiation and/or traffic level, that decisively influence and/or determine the temporal and spatial distribution and propagation of the pollutant emission (transmission) and hence the formation of the pollutant concentration, in particular at the location of the measurement station. In other words, the pollutant concentration measured for example at one time, or within a time range, by a measurement station is dependent on temperature, wind speed and/or traffic level and/or chemical substance concentrations in the air and/or solar radiation (watts per square meter). In principle, wind speed is a vector field that typically has a component that is horizontal and vertical relative to the earths surface. In the present case, subvariables of the wind speed, for example a wind direction (horizontal component), the absolute value of the wind speed and/or a wind strength (categorization into speed intervals), can likewise be used as measured variable. There may alternatively or additionally be provision for further physical/technical measured variables.

In some embodiments, the measurement series of the pollutant concentration and the measurement series of the measured variable were captured by means of a measurement station within a town. In some embodiments, high pollutant concentrations occur within cities and a large number of people are directly affected there. Measures to avoid high pollutant concentrations of this kind are therefore particularly necessary there. The teachings of the present disclosure can make a crucial contribution in this regard through improved prediction, which is made possible by a neural network trained in an improved manner.

In some embodiments, said measurement series are captured. In some embodiments, the transmission model used is a model which takes into account a chemical composition of the air and/or chemical reactions or conversion processes within the air. As a result, important chemical conversion processes, which can likewise be dependent on temperature, specific substance concentrations and/or solar radiation, in particular in the UV and/or optical range, can advantageously be taken into account. Furthermore, the pollutant emissions can likewise be determined by means of a domain model.

In some embodiments, the domain model comprises the traffic-specific pollutant emissions. In other words, the domain model can be used to compute the pollutant emissions of traffic, for example in an area of a town and/or on a road. The domain model therefore models the traffic-specific pollutant emissions.

In some embodiments, in a first step S1, a measurement series for a pollutant concentration $C_0(t)$, a temperature $T_0(t)$, a wind direction $W_0(t)$ and/or a wind speed $v(t)$ is provided. The pollutant concentration is a nitrogen oxide concentration, for example. The pollutant concentration and the measured variables, that is to say in the present case temperature, wind direction and/or wind speed, were captured jointly. With this in mind, the values of the measured variables are associated with the values of the pollutant concentration. As a result, for example four values are provided for each time, for example each hour of a day, namely the pollutant concentration for this time, the temperature for this time, the wind speed for this time and the wind direction for this time. It is possible to use average, averaged and/or weighted values for the respective time, for example over a time range of one hour, in this case. Furthermore, solar radiation and/or a chemical substance concentration could accordingly be determined.

In other words, by way of example, four time series $C_0(t)$, $T_0(t)$, $W_0(t)$, $v(t)$ are provided, wherein a measured value of the pollutant concentration, a measured value of the temperature, a measured value of the wind speed and a measured value of the wind direction are available for each time of the time series. The measured values do not have to have been captured at this time, but rather may have been selected or determined representatively for this time, for example by means of an averaging. By way of example, the time series comprise 24 values, which correspond to the hours in a day.

In a second step S2, the measured time series $T_0(t)$, $W_0(t)$, $v(t)$ of the measured variables and a pollutant emission determined by means of a domain model are used to compute a first pollutant immission $I_0$ by means of a transmission model, for at least one of the times t, e.g. for all times t. The first pollutant immission $I_0$ is therefore based on actual measured values, or measurement data. Temperature, wind direction and wind speed are typically relevant in this case.

In a third step S3, which can be carried out at the same time as S2, at least one value of at least one measured variable is altered. By way of example, the temperature prevailing at the time t is raised by 3 percent, and a new synthetic measurement series generated as a result. The thus freshly generated time series, or measurement series, has at least one value, which is based on this change and was accordingly not measured. With this in mind, the measurement series generated by the alteration is synthetic. A second pollutant immission $I_1$, for the time at which the measured value of the temperature was altered, is then computed from the unaltered time series for wind speed and wind direction and from the altered measurement series for temperature by means of the transmission model from the pollutant emissions which remain unaltered. The second pollutant immission $I_1$ is therefore based on actual measured values, or measurement data, and the measurement series generated synthetically by the alteration.

After steps S2 and S3, two pollutant immissions $I_0$, $I_1$ computed by means of the transmission model on the basis of the pollutant emission are therefore available for at least one time.

In a fourth step S4, the relative deviation $\Delta I/I_0 = (I_1 - I_0)/I_0$ in the computed pollutant immission is used to compute the relative change in the pollutant concentration by means of $\Delta C/C_0 = \alpha \Delta I/I_0$. In this case, $\alpha$ denotes the traffic-related proportion of the pollutant concentration. By way of example, $\alpha$ has the value 0.4.

The measurement series of the pollutant concentration is used to generate a new synthetic measurement series for the pollutant concentrations from the relative change in the pollutant concentration (at the time under consideration) by altering the measured value $C_0$ available at the time under consideration by $\Delta C$. This generates the new time series (synthetic measurement series), which can be used for training the neural network in addition to the originally provided measured measurement series of the pollutant concentrations. In principle, the approach described above can be taken for all times or parts of the times.

A simplified exemplary embodiment is outlined below. For a specific time and a specific location, for example the location or region of the measurement station, there is a high measured value for the nitrogen oxide concentration, that is to say a measured value above the threshold value or limit value. In this regard, a specific temperature, wind direction and wind speed are measured for this time.

The domain model specific to the pollutant emissions of traffic is used to compute the first pollutant emission for this time, for example 30 µg/m/s of nitrogen oxides, for the measured temperature, wind direction and wind direction and/or traffic density/traffic level (input variables or input parameters of the domain model).

Based on the computed pollutant emission, a first pollutant immission is determined at the measurement station by means of the transmission model. A further computation using a slightly altered temperature, for example raised by 5 percent or 5 degrees Celsius compared to the originally measured temperature, is then performed using the transmission model. The wind speed and the wind direction remain unaltered in this case. This yields the second pollutant immission, for example 33 µg/m/s of nitrogen oxides. As a result, a relative change in the pollutant immission by 10 percent is obtained. This relative change in the pollutant immission is now transferred, or converted, to a relative change in the pollutant concentration (at the measurement station).

The pollutant concentration typically comprises multiple proportions, for example a traffic proportion (traffic-related proportion), a buildings proportion and a proportion from power generation. By way of example, the traffic-related proportion $\alpha$ is equal to 44 percent, the buildings-related proportion or region-related proportion is 18 percent and the power-generation-related proportion is 38 percent. In particular the traffic-related proportion has been falling, in terms of nitrogen oxides, for years and will probably reduce further in the coming years.

From the traffic-related proportion, it is then possible to infer the relative change in the pollutant concentration by virtue of $\Delta C/C_0 = \alpha \Delta I/I_0$. A relative change in the pollutant immission by 10 percent therefore results in a relative change in the pollutant concentration by 4.4 percent. That is to say that the originally measured pollutant concentration would change by 4.4 percent at the time under consideration in the present case. In other words, a 10 percent change in the temperature or a change in the temperature by 5 degrees Celsius translates into a 4.4 percent change in the pollutant concentration.

If the method outlined above is carried out for each time or for further selected times of the measured time series for the pollutant concentrations, a new synthetic time series, or measurement series, for the pollutant concentration can be generated. The neural network can then be trained using this freshly generated time series.

The described example method is computer aided and can be carried out using a computer, a central or decentralized server, in the cloud or by means of a quantum computer. Furthermore, the computer aided method is based on measured values of physical measured variables that are included as input variables, or input parameters.

Although the teachings herein have been illustrated and described more thoroughly in detail by means of the preferred exemplary embodiments, the scope of the disclosure is not restricted by the disclosed examples, or other variations can be derived therefrom by a person skilled in the art without departing from the scope of protection of the present disclosure.

LIST OF REFERENCE SIGNS

S1 first step
S2 second step
S3 third step
S4 fourth step

What is claimed is:

1. A computer aided method for generating training data to train a neural network designed to determine pollutant concentration at a measurement station from pollutant emission, the method comprising:
   providing a measurement series of pollutant concentration containing a measured value of pollutant concentration above a defined threshold value;
   providing a measurement series for a physical variable related to the measured value of pollutant concentration and containing a measured value of the physical variable;
   providing a transmission model modelling a relationship between pollutant emission, the physical variable, and pollutant immission at the measurement station;
   computing a first value of pollutant immission using the transmission model, wherein a pollutant emission value and the measured value of the physical variable related to the measured value of pollutant concentration are provided as inputs to the transmission model to compute the first value;
   computing a second value of pollutant immission using the transmission model, wherein the pollutant emission value and a numerical alteration of the measured value of the physical variable used for computing the first value of pollutant immission are provided as inputs to the transmission model to compute the second value;
   generating a synthetic measurement series as the training data using a numerical alteration of the measured value of pollutant concentration of the measurement series of pollutant concentration, the numerical alteration based at least in part on a relative change between the first and second computed values of pollutant immission; and
   training the neural network using the training data.

2. The computer aided method as claimed in claim 1, wherein the numerical alteration of the measured value of pollutant concentration of the measurement series of pollutant concentration depends at least in part on a traffic-related proportion of the pollutant concentration.

3. The computer aided method as claimed in claim 2, wherein the numerical alteration of the measured value of pollutant concentration of the measurement series of pollutant concentration is based on $\Delta C/C_0 = \alpha \Delta I/I_0$, where $C_0$ is the measured value of pollutant concentration of the measurement series of pollutant concentration, $I_0$ is the first computed value of pollutant immission, $\Delta I$ is the relative change between the first and second computed values of pollutant immission, $\alpha$ is the traffic-related proportion of the pollutant concentration, and $\Delta C$ is a difference between $C_0$ and the numerical alteration of the measured value of pollutant concentration of the measurement series of pollutant concentration.

4. The computer aided method as claimed in claim 2, wherein the traffic-related proportion of the pollutant concentration has a value in a range from 0.3 to 0.5.

5. The computer aided method as claimed in claim 1, further comprising using a nitrogen oxide concentration as pollutant concentration and a nitrogen oxide emission as pollutant emission.

6. The computer aided method as claimed in claim 1, wherein the physical variable comprises one or more variables selected form the group consisting of: a temperature, a wind speed, a traffic level, and a chemical substance concentration.

7. The computer aided method as claimed in claim 1, wherein the measurement series of pollutant concentration and the measurement series for the physical variable are captured by means of a measurement station within a town.

8. The computer aided method as claimed in claim 1, wherein the transmission model comprises a model based on a chemical composition of air and/or chemical reactions within the air.

9. A computer aided method for determining a pollutant concentration using the trained neural network of claim 1 and a domain model of pollutant emission, wherein the neural network determines the pollutant concentration from an input pollutant emission, wherein the domain model models a relationship between a physical variable and pollutant emission, the method comprising:
   computing a value of pollutant emission using a measured value of the physical variable as input to the domain model; and
   determining a value of the pollutant concentration by using the computed value of the pollutant emission as the input pollutant emission to the trained neural network.

* * * * *